(12) United States Patent
Karicherla et al.

(10) Patent No.: US 7,551,967 B1
(45) Date of Patent: Jun. 23, 2009

(54) IMPLANTABLE MEDICAL LEADS AND DEVICES HAVING CARBON NANOTUBE-BASED ANTI-ELECTROSTATIC COATINGS AND METHODS FOR MAKING SUCH LEADS AND DEVICES

(75) Inventors: Annapurna Karicherla, Valencia, CA (US); Buehl E. Truex, Glendora, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 254 days.

(21) Appl. No.: 11/133,921

(22) Filed: May 19, 2005

(51) Int. Cl.
*A61N 1/39* (2006.01)
(52) U.S. Cl. .................. 607/122; 600/374
(58) Field of Classification Search ............ 607/36, 607/118–132; 600/373–374
See application file for complete search history.

(56) References Cited

U.S. PATENT DOCUMENTS

| | | | | |
|---|---|---|---|---|
| 6,528,572 B1 * | 3/2003 | Patel et al. | ............... | 524/495 |
| 6,673,999 B1 | 1/2004 | Wang et al. | ............... | 174/36 |
| 6,713,671 B1 | 3/2004 | Wang et al. | ............... | 174/35 |
| 6,999,821 B2 * | 2/2006 | Jenney et al. | ............... | 607/122 |
| 7,039,465 B2 * | 5/2006 | Bardy et al. | ............... | 607/36 |
| 7,162,308 B2 * | 1/2007 | O'Brien et al. | ............... | 607/116 |

FOREIGN PATENT DOCUMENTS

WO  WO 2003/061755 A2  7/2003
WO  WO 2003/061755 A3  7/2003

OTHER PUBLICATIONS

Baughman, Ray H. et al., Carbon Nanotubes—the Route Toward Applications, *Science*, vol. 297 (Aug. 2, 2002), pp. 787-792.
Colbert, Daniel T., Single-Wall Nanotubes: A New Option for Conductive Plastics and Engineering Polymers, *Plastics Additives & Compounding* (Jan./Feb. 2003).
Yumura, Motoo, *Carbon Nanotube Industrial Applications*, AIST Today International Edition No. 10 (Oct. 2003), pp. 8-9.

* cited by examiner

*Primary Examiner*—Mark W Bockelman

(57) ABSTRACT

An implantable medical lead for transmitting electrical signals between an implantable medical device and selected body tissue comprises a lead body having a distal end portion, a proximal end and an electrically insulating, elongated housing connecting the distal end portion and the proximal end. The proximal end of the lead body carries an electrical connector assembly adapted to be electrically connected to the implantable medical device and the distal end portion of the lead body carries at least one electrode electrically coupled to a terminal contact on the connector assembly. The lead comprises at least one surface susceptible during use of the lead to the accumulation of electrostatic charges, the at least one surface having a coating comprising carbon nanotubes.

5 Claims, 5 Drawing Sheets

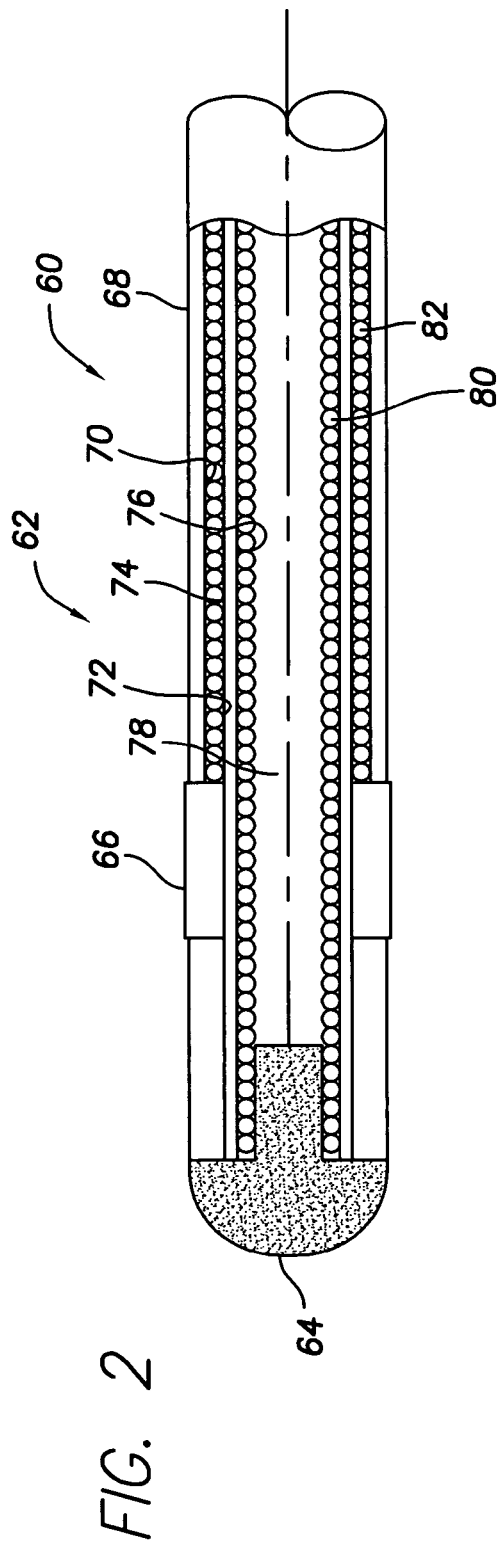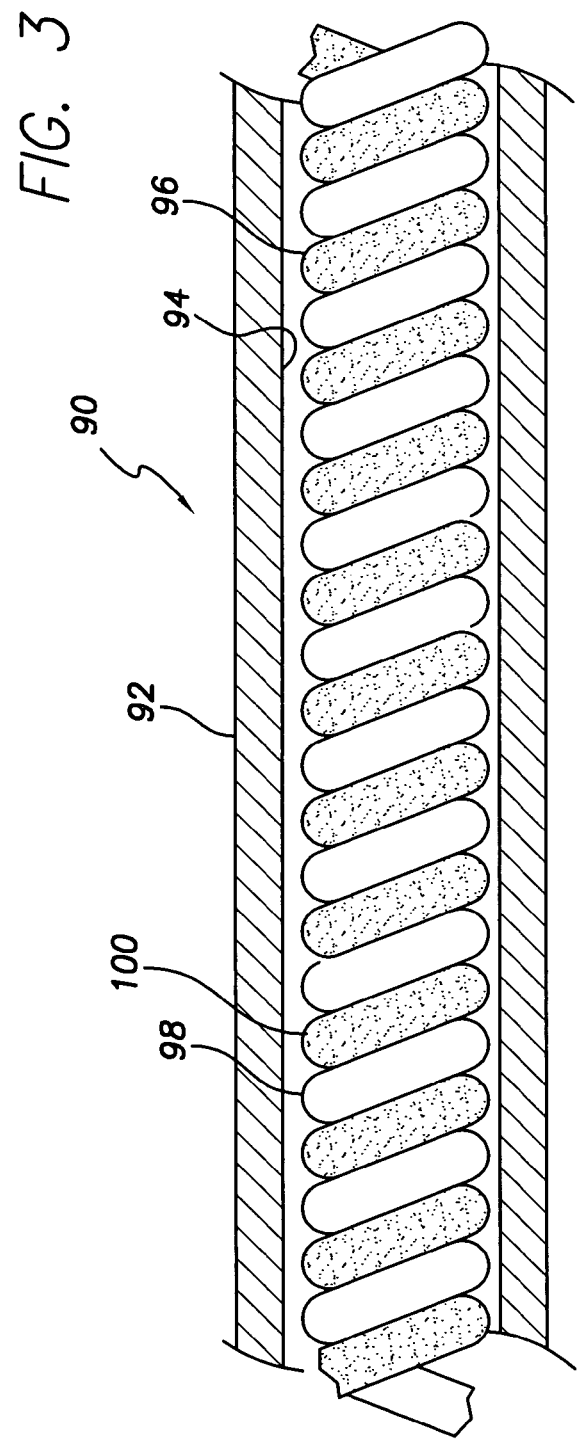

IMPLANTABLE MEDICAL LEADS AND DEVICES HAVING CARBON NANOTUBE-BASED ANTI-ELECTROSTATIC COATINGS AND METHODS FOR MAKING SUCH LEADS AND DEVICES

FIELD OF THE INVENTION

The present invention relates generally to implantable medical devices, and particularly to implantable medical leads having one or more surfaces treated to prevent the accumulation of electrostatic charges or to dissipate such charges.

BACKGROUND OF THE INVENTION

Body implantable electrical leads form the electrical connection between an implantable medical device (IMD), such as a cardiac pacemaker and/or implantable cardioverter-defibrillator (ICD), and body tissue, such as that of the heart, which is to be electrically stimulated. As is well known, the leads connecting IMDs with the heart may be used for pacing or for sensing electrical signals produced by the heart, or for both pacing and sensing in which case a single lead serves as a bidirectional pulse transmission link between the pacemaker and the heart. An endocardial type lead, that is, a lead that is inserted into a vein and guided therethrough into a cavity of the heart, comprises a lead body that carries along its distal end portion one or more electrodes designed to contact the endocardium, the tissue lining the inside of the heart. The lead body further includes a proximal end carrying an electrical connector assembly adapted to be received by the IMD. By way of example, the connector assembly may be of the trifurcated type comprising first and second connector branches that may conform to the DF-1 standard for supplying electrical impulses to shocking electrodes, and a third connector branch that may conform to the IS-1 standard for connecting the IMD to a tip electrode and a ring electrode. Alternatively, the connector assembly may simply comprise a single in-line or coaxial connector of the IS-1 type or conforming to the proposed quadripole IS-4 or DF-4 standard. The IS-4 and DF-4 connector assemblies are less bulky than trifurcated assemblies and comprise a coaxially arranged pin terminal contact and three ring terminal contacts. A flexible cable or coil conductor surrounded by an insulating sheath or housing of a polymer such as silicone rubber or polyurethane electrically connects each terminal contact on the electrical connector assembly with an associated electrode on the distal end portion of the lead.

The generation of static electricity caused by rubbing two substances together is called the triboelectric effect. The prime sources of static electricity are insulators typically made of synthetic materials. Voltage levels generated by these insulating sources can be extremely high since their charges are not readily dissipated or distributed over their surfaces or conducted to other objects. The accumulation of electrostatic charge in the form of rubbing, friction-induced triboelectric charge has been a persistent problem with endocardial leads. Such charges may accumulate, for example, as a result of the electrical conductor coils rubbing against the surfaces of the insulating housing of the lead body such as the walls of the conductor—containing lumen(s) inside the housing.

Static charge build-ups have also been observed on the in-line, quadripole connector assemblies conforming to the proposed DF-4 standard. These connector assemblies typically include a pair of high voltage ring terminal contacts that supply dual shock electrodes. Static charges tend to build up on the insulation between and adjacent to the ring terminal contacts on the connector assembly as a result of the high voltage spikes during defibrillation. The electrical insulation may slowly degrade (similar to being electrically burned) due to the voltage build-up. Similarly, static charges tend to build up on the surfaces of the internal insulating seals between the contact elements within the connector assembly-receiving cavity in the IMD and to progressively burn away these seals.

The dissipation of electrostatic charges is a particular problem in leads carrying cardiomechanical sensors (CMES) such as pressure transducers or accelerometers that generate very low amplitude output signals that are easily lost in the noise produced by the static charges.

Antistatic coatings applied to the charge-accumulating surfaces of lead body housings and connector assemblies have been used to dissipate static charge or to prevent their buildup. These coatings typically comprise polymers filled with low aspect ratio graphite particles, carbon fibers, carbon black, or the like, that render the coatings sufficiently electrically conductive so as to dissipate charge. Such charge dissipation can occur, however, only if the loading levels of the filler materials are high enough to produce percolation, that is, extended, connected networks providing sufficient electrical conductivity. Thus, these coatings tend to be relatively thick and therefore unacceptable for use with leads having small diameters, and with connector assemblies such as the aforementioned DF-4 connector assembly that is small and has tight design tolerances.

SUMMARY OF THE INVENTION

In accordance with one specific, exemplary embodiment of the invention, there is provided an implantable medical lead for transmitting electrical signals between an implantable medical device and selected body tissue. The lead comprises a lead body comprising a distal end portion, a proximal end and an electrically insulating, elongated housing connecting the distal end portion and the proximal end. The proximal end of the lead body carries an electrical connector assembly adapted to be electrically connected to the implantable medical device and the distal end portion of the lead body carries at least one electrode electrically coupled to a terminal contact on the connector assembly. The lead comprises at least one surface susceptible during use of the lead to the accumulation of electrostatic charges, the at least one surface having a coating sufficiently conductive electrically to dissipate any such accumulated charges, the coating comprising carbon nanotubes.

In accordance with another aspect of the invention, the housing comprises at least one lumen extending between the distal end portion and the proximal end of the lead body, the lumen containing an electrical conductor electrically coupling the at least one electrode to the terminal contact on the connector assembly, the at least one surface comprising at least a portion of a wall defining the at least one lumen. The electrical conductor may comprise a coil conductor, or, the electrical conductor may comprise a cable conductor.

Pursuant to another aspect of the invention, the at least one surface may comprise at least a portion of an insulating sealing surface on the electrical connector assembly. In one form of the invention, the connector assembly may conform to the IS-4 standard. In another form of the invention, the connector assembly may conform to the DF-4 standard.

According to yet another aspect of the invention, the coating may comprise a matrix selected from the group consisting of butylene tere phthalate, polyurethane, polystyrene, polyurethane/silicone copolymers and blends, and silicones, the carbon nanotubes being dispersed in the matrix. Other similar materials could also be used for the matrix, the requirement being good dispersion of the carbon nanotubes in the matrix. Still further, preferably, the coating may comprise a carbon nanotube loading of 0.005% to 4.5%, by weight; generally, the lowest loading providing the required electrostatic dissipation properties is most preferred.

In accordance with another specific, exemplary embodiment of the invention, there is provided a system for electrically stimulating body tissue and/or sensing electrical potentials generated by the tissue. The system comprises an implantable medical lead comprising a lead body including a distal end portion, a proximal end and an electrically insulating, elongated housing connecting the distal end portion and the proximal end, the proximal end carrying an electrical connector assembly containing an electrical terminal contact electrically connected to an electrode on the distal end portion of the lead body. The system further comprises an implantable medical device defining a receptacle for receiving the connector assembly, the receptacle containing an electrical contact adapted to be engaged by the terminal contact on the connector assembly. In addition, the system comprises at least one insulating surface susceptible of accumulating electrostatic charges, the at least one insulating surface having a coating sufficiently conductive electrically to dissipate any such accumulated charges, the coating comprising carbon nanotubes.

Pursuant to one form of the system, the at least one insulating surface may comprise the surface of an internal, insulative seal means within the receptacle defined by the implantable medical device. Alternatively, or in addition thereto, the at least one insulating surface may comprise a sealing surface disposed adjacent to the electrical terminal contact on the connector assembly. As a further alternative thereto, or further in addition thereto, the at least one insulating surface may comprise the wall of a lumen defined by the housing, the lumen containing an electrical conductor connecting the electrical terminal contact on the connector assembly with the electrode on the distal end portion of the lead.

In accordance with yet another embodiment of the invention, there is provided an implantable medical device having a receptacle for receiving the connector assembly of an implantable medical lead. The receptacle includes at least one insulating sealing surface carrying a coating sufficiently conductive electrically to dissipate electrostatic charges accumulating on the surface, the coating comprising carbon nanotubes. In one form of the device, the insulating sealing surface is defined by an internal seal means.

Pursuant to another exemplary embodiment of the invention, there is provided in a method for fabricating an implantable medical lead having an elongated insulative housing comprising at least one lumen containing an electrical conductor electrically connecting an electrode on a distal end portion of the lead with a terminal contact on a proximal end of the lead, the step of applying to the wall of the lumen an anti-static coating comprising carbon nanotubes.

According to yet another embodiment of the invention, there is provided in a method of fabricating an implantable medical lead having a distal end portion carrying at least one electrode electrically connected with a terminal contact on a connector assembly attached to a proximal end of the lead, the connector assembly comprising at least one insulative sealing surface, the step of applying to the at least one insulative sealing surface of the connector assembly an anti-static coating comprising carbon nanotubes.

BRIEF DESCRIPTION OF THE DRAWINGS

FIG. 2 is a side view, partly in cross section, of the distal end portion of a pacing lead in accordance with another embodiment of the invention;

FIG. 3 is a side view, partly in cross section, of a portion of the lead body of a bipolar pacing lead in accordance with yet another embodiment of the invention;

DETAILED DESCRIPTION

The following description is of a best mode presently contemplated for practicing the invention. This description is not to be taken in a limiting sense but is made merely for the purpose of describing the general principles of the invention whose scope is defined by the appended claims. Although the invention will be described in the context of implantable cardiac stimulation and sensing leads, it will be evident to those skilled in the art that the invention described herein has broader utility, being applicable to a wide variety of implantable medical leads for stimulating selected body tissue and sensing the electrical activity of such tissue.

Figure 1:
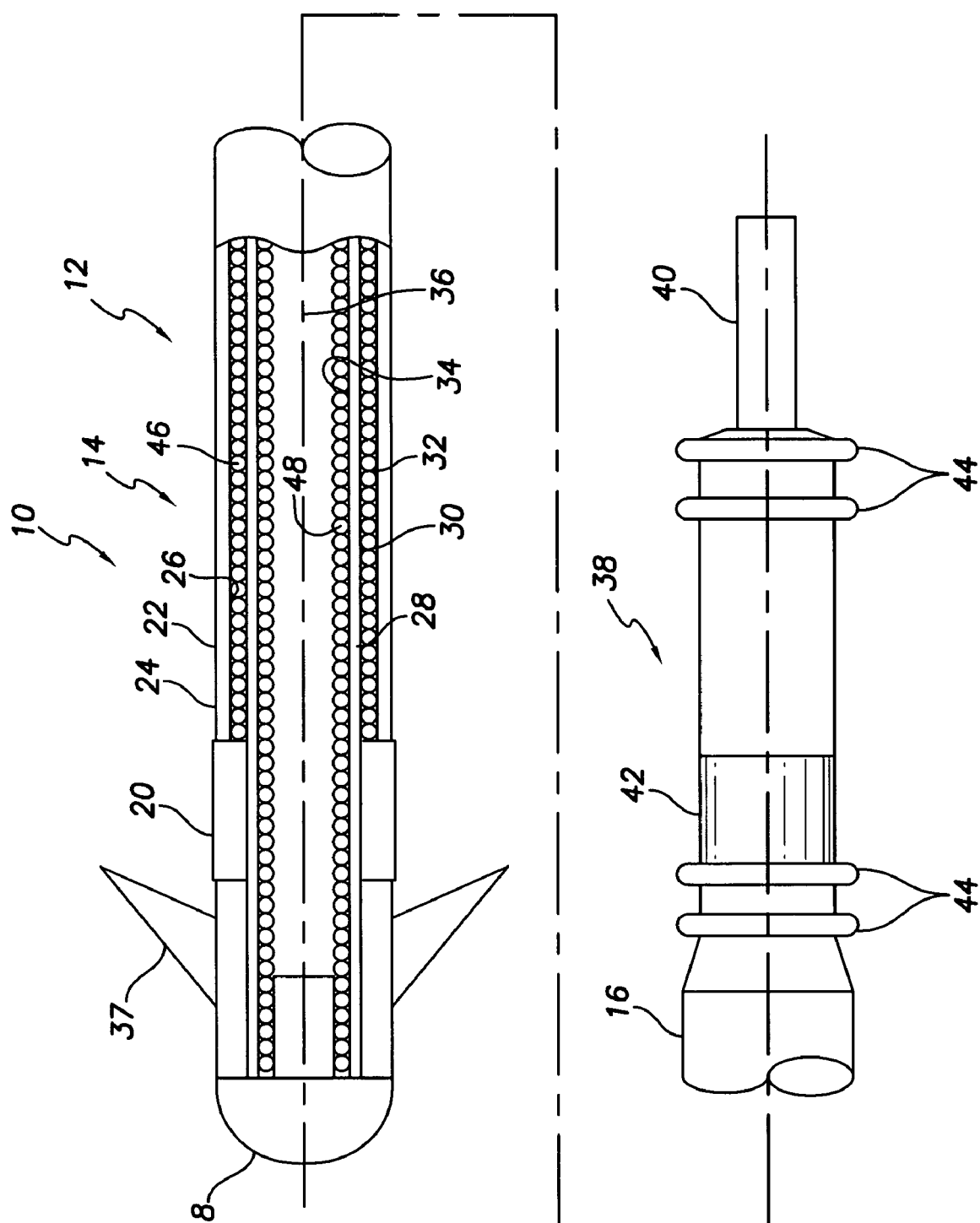
FIG. 1 is a side view, partly in cross section, of a portion of a bipolar, endocardial pacing lead in accordance with one embodiment of the invention.

FIG. 1 shows in simplified, schematic form an endocardial, passive-fixation, body implantable lead 10 in accordance with a first embodiment of the invention. The lead 10 includes a lead body 12 having a distal end portion 14 and a proximal end 16. The distal end portion 14 includes a tip electrode 18 and a ring electrode 20 positioned proximally of the tip electrode. As is well known in the art, the combination of the tip and ring electrodes typically provide bipolar pacing and sensing functions. The lead body 12 includes an outer, tubular sheath or housing 22 of a suitable insulating, biocompatible, biostable material such as, for example, silicone rubber or polyurethane, extending substantially the entire length of the lead body. The insulating housing 22 has an outer surface 24 and an inner surface 26. Positioned coaxially within the outer housing 22 is an inner insulating sleeve 28 of, for example, silicone rubber, having an outer surface 30 defining with the inner surface 26 of the outer housing an annular space 32. The sleeve 28 further has an inner surface 34 defining a central passage or lumen 36.

In conventional fashion, the distal end portion 14 of the lead body 12 may include passive fixation means that may take the form of projecting tines 37 for anchoring the lead body within a chamber of the heart. Alternatively or in addition thereto, the passive fixation or anchoring means may comprise one or more preformed humps, spirals, S-shaped bends, or other configurations manufactured into the distal end portion of the lead body 12 where the lead is intended for left heart placement within a vessel of the coronary sinus region. The fixation means may also comprise an active fixation mechanism such as a helix. It will be evident to those skilled in the art that any combination of the foregoing fixation or anchoring means may be employed.

The proximal end 16 of the lead body carries an in-line or coaxial connector assembly 38 that, by way of example, may conform to the medical device industry's IS-1 standard and that comprises a tubular pin terminal contact 40 and a ring terminal contact 42. The connector assembly 38 is adapted to be received within a cavity or receptacle of an implantable medical device (IMD) (not shown) such as a pulse generator or pacemaker. The receptacle contains contacts for electrically engaging the pin and ring terminal contacts 40 and 42 on the connector assembly 38. Spaced apart seals 44 on the connector assembly prevent short-circuiting bodily fluids from entering the receptacle of the IMD.

The ring electrode 20 is electrically connected to the ring terminal contact 42 by means of a first coil conductor 46 disposed within the annular space 32 between the outer housing and the inner sleeve. The tip electrode 18 is electrically connected to the pin terminal contact 40 by means of a second or inner coil conductor 48 carried within the lumen 36 of the inner sleeve 28. In accordance with standard implantation techniques, a stylet or guide wire (not shown) for delivering and steering the distal end portion of the lead body 12 during implantation is inserted into the lumen of the coil conductor 48 through the tubular terminal pin 40. It will be evident that a substantial portion of the length of the inner coil conductor 48 will tend to ride in contact with the inner surface 34 of the sleeve and to move relative thereto in rubbing fashion during use of the implanted lead. A similar rubbing action will tend to occur between the outer coil conductor 46, on the one hand, and the confronting surfaces 26 and 30 of the outer housing 22 and the inner sleeve 28, on the other. These relative rubbing movements often generate static charges on the surfaces of the insulating housing and sleeve. Such static charges may interfere with or mask the low amplitude electrical potentials generated by the body tissue, such as cardiac musculature, in electrical communication with the tip and ring electrodes and sensed by those electrodes.

In accordance with the present invention, at least one of the insulating surfaces 26, 30 and 34, and preferably all of such surfaces, is coated with an anti-static or electrostatic dissipative, carbon nanotube composition which may comprise, by way of example and not limitation, a loading of 0.005% to 4.5%, by weight, of carbon nanotubes dispersed in a biocompatible, biostable polymer matrix such as polyurethane, butylene tere phthalate, silicones, polyurethane/silicone copolymers and blends, and polystyrene. Various nanotube types may be used, including multiwalled nanotubes, single walled nanotubes, double walled nanotubes, carbon ropes, and so forth, available from such suppliers as CarboLex, Mitsui, Nanoledge and Hyperion, the latter providing carbon nanotubes predispersed in a resin. More preferably, the coating may comprise 0.005%, by weight, carbon nanotube loading in a biocompatible, biostable matrix that is compatible with the lead design. Generally, the coating preferably comprises the lowest carbon nanotube loading in a biocompatible, biostable matrix that achieves dispersion of electrostatic charge.

The carbon nanotubes are highly conductive and therefore a very small loading of this material in a polymer such as those described above is sufficient to dissipate a build up of static charges, compared to the materials like graphite and carbon black. This reduction in filler loading increases the flowability of the coating, facilitating the use of multiple coating techniques such as spraying or painting. Coating complex shapes and accessing difficult regions of a component are easier with a flowable, easy-to-handle carbon nanotube-based coating. Furthermore, the nanotube-based coating is extremely thin compared with other coatings and this helps to keep the lead size and tolerances within acceptable limits.

This composition is sufficiently conductive to prevent the accumulation of triboelectric charges along the surfaces to which it is applied, or to dissipate any such electrostatic charges that may have accumulated. Accordingly, any one or more of the surfaces 26, 30, and 34 may be treated in this fashion.

It will be evident that the present invention is equally applicable to a wide variety of lead designs, configurations and functions. For example, FIG. 2 shows a portion of an endocardial lead body 60 having a distal end portion 62 carrying a tip pacing and/or sensing electrode 64 together with—instead of or in addition to one or more ring electrodes—an annular cardiomechanical transducer 66 for sensing such physiological parameters as pressure or acceleration. As before, the lead body comprises an insulating, outer tubular housing 68 having an inner surface 70, and an inner, insulating sleeve 72 having an outer surface 74 and an inner surface 76 defining a central lumen 78. The tip electrode 64 is electrically coupled to a terminal contact on a proximal end of the lead body by means of a coil conductor 80 within the lumen 78. The output of the transducer 66, transmitted to a ring terminal contact on a connector assembly by a conductor, such as the coil conductor 82, typically has a small amplitude that, in the absence of the anti-static treatment afforded by the present invention, might be lost in or masked by electrical noise generated by the static charge. Thus, preferably all of the surfaces 70, 74 and 76 are coated with a carbon nanotube composition such as that described earlier.

FIG. 3 illustrates another embodiment of the present invention. FIG. 3 shows an axial cross-section view of a portion of a lead body 90 comprising a tubular, insulating sheath or housing 92 made of an insulating biocompatible, biostable material such as silicone rubber or polyurethane. The lead configuration may be similar to that shown in FIG. 1, namely, one comprising a distal end portion carrying a tip electrode and a ring electrode positioned proximally of the tip electrode. Similarly, the proximal end of the lead body may carry an in-line or coaxial connector assembly such as that shown in FIG. 1. The housing 92 has an inner surface 94 defining a central lumen or passage 96 containing a pair of coil conductors 98 and 100 for electrically connecting the tip and ring electrodes along the distal end portion of the lead with corresponding terminal contacts on the connector assembly at the proximal end of the lead body. Each of the coil conductors 98 and 100 has an insulating coating so that the conductors may be wound so as to have substantially the same outer diameter. Such a co-radial coil conductor configuration has the advantage of reducing the outer diameter of the lead body 90.

Relative rubbing motion between the insulated coil conductors 98 and 100 and the inner surface 94 of the insulating housing 92 may result in the accumulation of triboelectric charges on the surfaces of these insulating elements. To prevent the accumulation of such charges or to dissipate any such charges that may have accumulated, either or both the inner surface 94 of the housing 92 and the outer surfaces of the insulated coil conductors 98 and 100 are, in accordance with the invention, coated with a carbon nanotube composition as previously described. As explained, in the absence of such an anti-static coating, the useful signal, which is typically extremely small, will often be lost in the disturbance or noise generated by the static charge.

Figure 4:
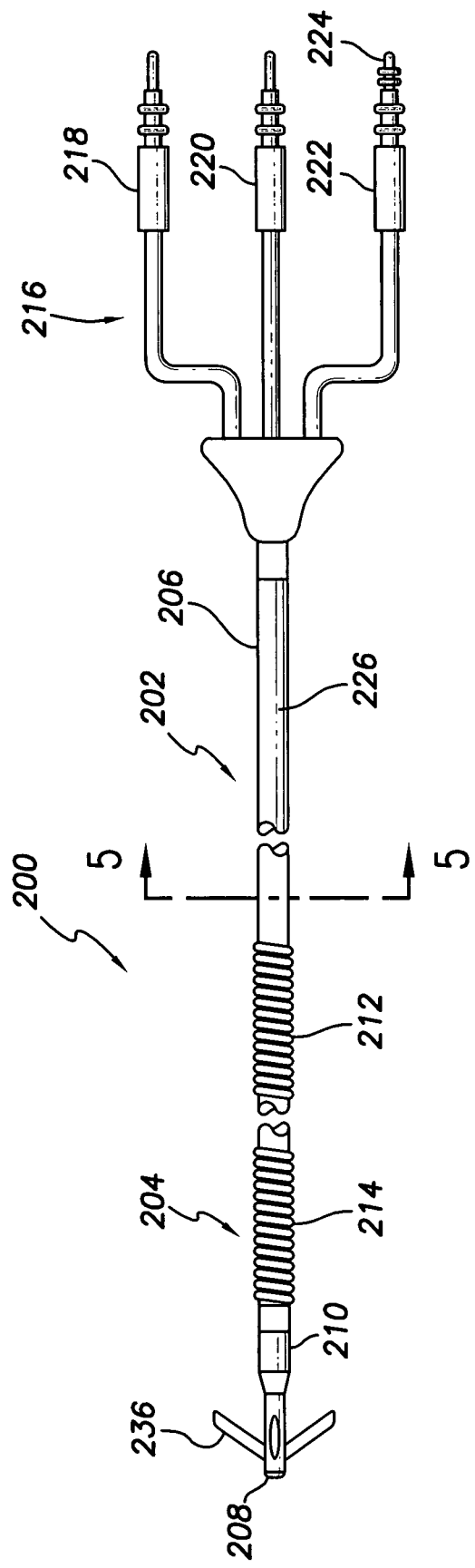
FIG. 4 is a side view of a dual shocking electrode, bipolar pacing lead in accordance with still a further embodiment of the invention.
Figure 5:
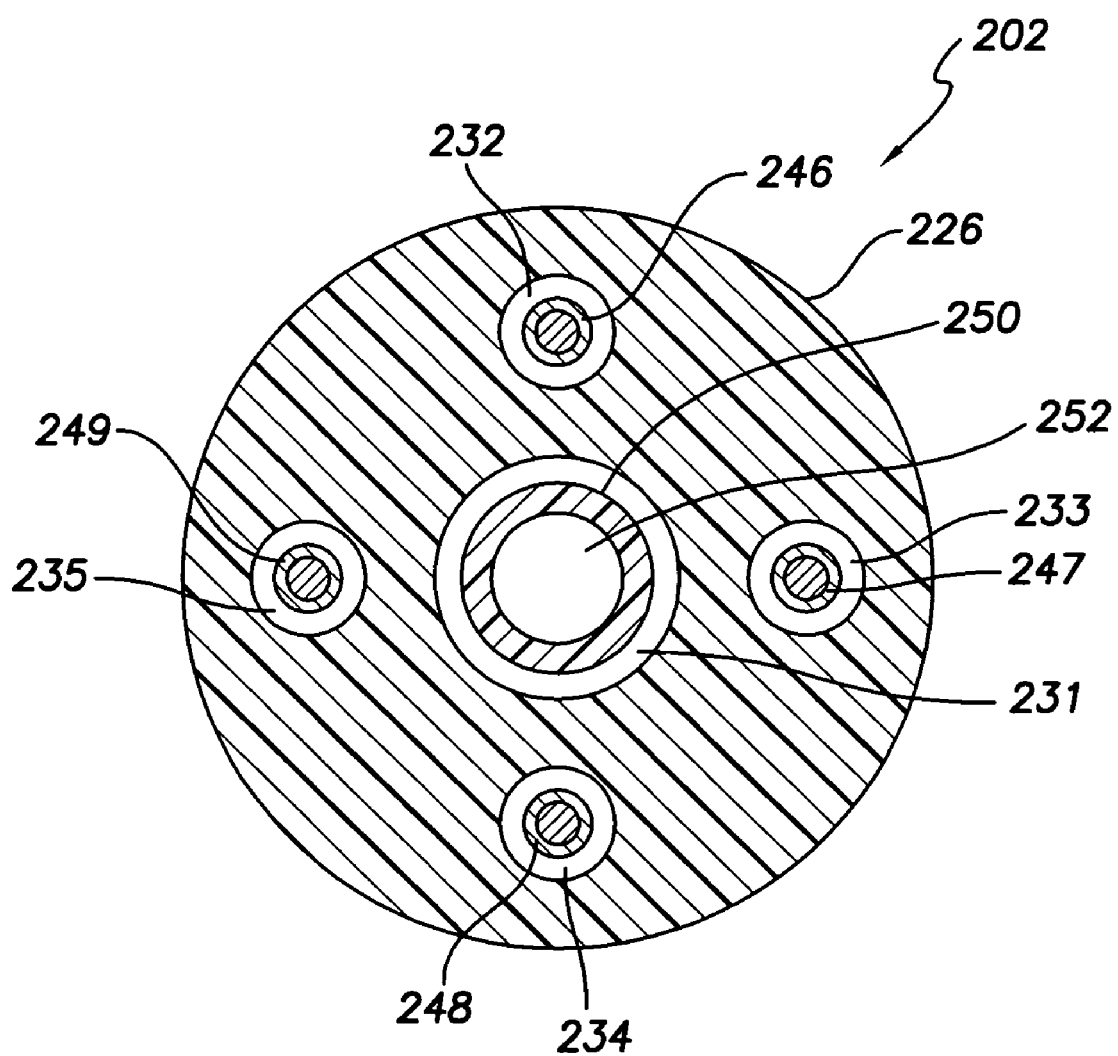
FIG. 5 is a transverse, cross section view of the lead of FIG. 4 as seen along the line 5-5 in FIG. 4.

Turning now to FIGS. 4 and 5, there is shown a dual shock, bipolar pacing lead 200 along with certain details thereof, in accordance with an alternative embodiment of the present invention. The lead 200 includes a lead body 202 having a distal end portion 204 and a proximal end 206. The distal end portion 204 includes a tip electrode 208, a ring electrode 210, and two spaced-apart, shocking electrodes comprising a proximal shocking electrode 212 and a distal shocking electrode 214. The proximal shocking electrode 212 may be positioned so as to stimulate the SVC while the distal shocking electrode 214 may be disposed to shock the right ventricle.

The proximal end 206 of the lead body includes a trifurcated connector assembly 216 for coupling the lead to an IMD, for example, a pacemaker/defibrillator unit (not shown). The trifurcated connector assembly 216 comprises first and second connectors 218 and 220 that may conform to the DF-1 standard for supplying electrical impulses to the shocking electrodes 212 and 214 and a third connector 222 that may conform to the IS-1 standard for connecting the pacemaker/defibrillator unit to the tip and ring electrodes 208 and 210. The third connector 222 includes a tubular connector pin 224.

The lead body 202 comprises an insulating sheath or housing 226 made of a suitable insulating, biocompatible, biostable material such as, for example, silicone rubber or polyurethane. Although the tubular housing may have various cross-sectional configurations, in accordance with the embodiment of FIGS. 4 and 5, the housing 226 comprises a multilumen structure. More specifically, the housing defines five axially extending parallel lumens 231-235 including a relatively large central lumen 231 surrounded by four, symmetrically disposed smaller lumens 232-235 of equal diameter. It will be understood that suitable anchoring means may be provided such as outwardly projecting tines 236, by themselves or in combination with one or more S-shaped bends, along the distal end portion 204 of the lead for anchoring in the vessels of the coronary sinus region.

The lumens 232-235 defined by the housing 226 carry electrical conductors 246-249, respectively, for connecting the electrodes 208, 210, 212 and 214 to the corresponding terminal contacts on the connector assembly. These conductors may comprise coil or cable conductors. The central lumen 231 may carry a thin-walled polymer tube 250 providing a low friction passageway 252 for a stylet or guide wire (not shown) used to maneuver the distal end portion 204 of the lead to its target location. Relative movements between the various elements may cause accumulation of static charges. In accordance with the invention, the wall of each of the lumens 231-235 is coated with an anti-static nanotube composition, as described, to dissipate or prevent the accumulation of triboelectric charges.

Figure 6:
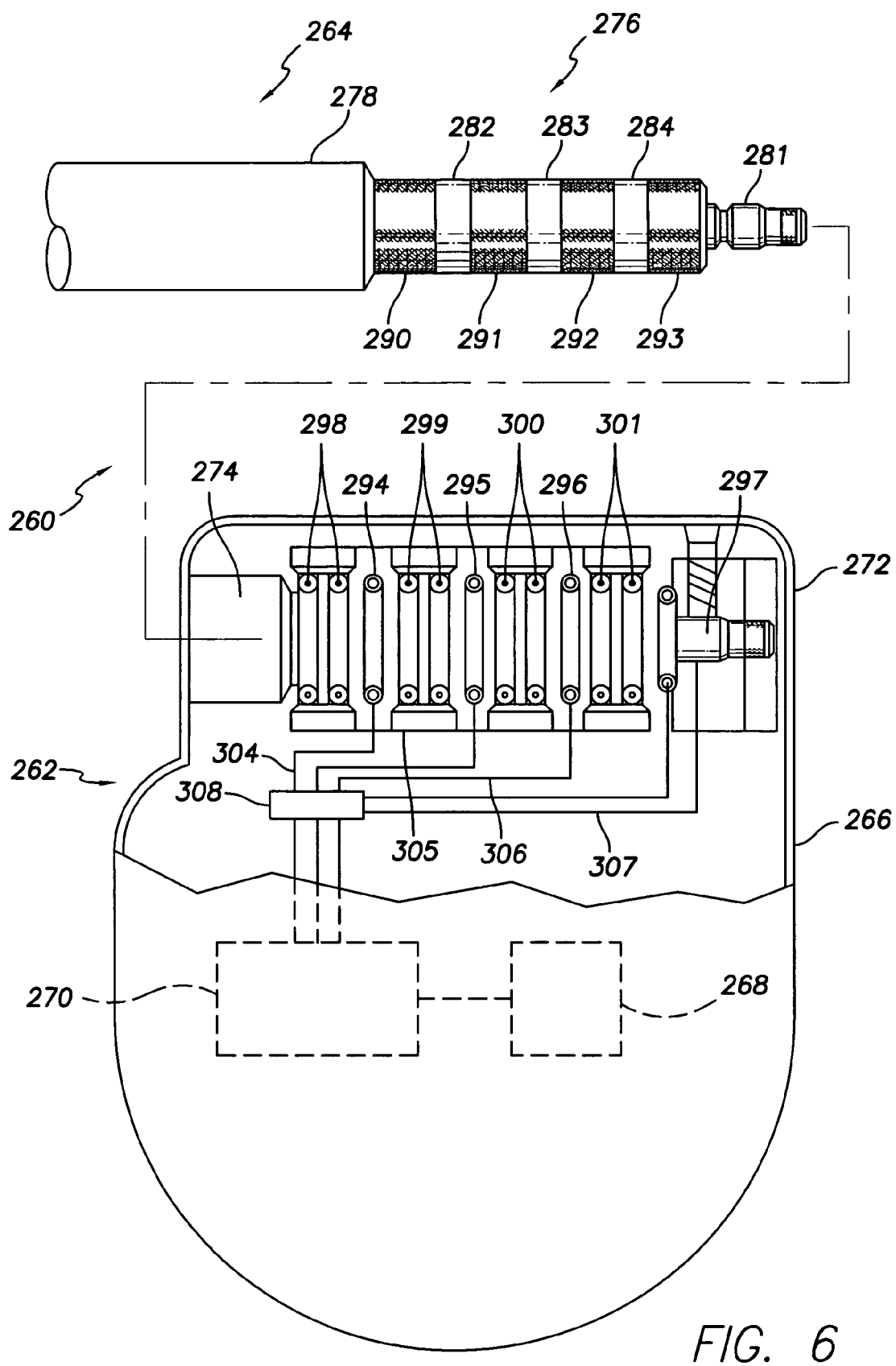
FIG. 6 is a side view of a portion of a quadripole lead system incorporating the present invention.

FIG. 6 shows a system 260 for electrically stimulating selected body tissue. The system 260 incorporates a specific, exemplary embodiment of the invention and basically comprises an IMD 262 that may take the form of a pacemaker/ICD and an associated electrical lead 264 that may comprise a dual shock, bipolar pacing and sensing lead.

The IMD 262 comprises a pulse generator that includes a hermetically sealed metallic enclosure 266 containing a power supply 268 (typically a battery), electronic circuitry 270 and an attached header 272 having at least one receptacle 274 for receiving an in-line, coaxial electrical connector assembly 276 attached to a proximal end 278 of the lead 264. The connector assembly 276, in the example under consideration, conforms to the proposed DF-4 standard. The header 272 may be either integral with the enclosure 266 or formed as a separate element and attached to the enclosure. Generally, when the header 272 is formed as a separate element, it is molded from epoxy material. Although the header 272 is shown for simplicity as a single molded piece, in practice the header or a portion thereof, such as a sleeve, defining the receptacle 272 will typically be made of a plurality of appropriately joined, individually molded parts.

The lead 264 may comprise a distal end portion carrying a tip electrode, a ring electrode proximal of the tip electrode and a pair of shocking electrodes, along the lines of that shown, for example, in FIG. 4. The in-line electrical connector assembly 276 includes a low voltage pin terminal contact 281 electrically connected to the tip electrode, a pair of high voltage ring terminal contacts 282 and 283 connected to the shocking electrodes and a low voltage ring terminal contact 284 electrically connected to the ring electrode. These connections are implemented by means of coil or cable conductors enclosed within the lead housing as shown, for example, in FIG. 5. The connector assembly 276 further comprises insulative sealing surfaces 290-293 alternating with the ring terminal contacts. When the connector assembly 276 is fully inserted into the receptacle 274, electrical connections are established between the ring terminal contacts 282-284 on the connector assembly 276 and corresponding resilient contacts 294-296 within the receptacle. These contacts may comprise garter spring contacts well known in the art. Internal seal sets 298-301 cooperating with the sealing surfaces 290-293 on the connector assembly prevent the entry of body fluids into the receptacle. The pin terminal contact 281 engages a contact 297 within the receptacle 274. The electrical contacts 294-297 are in turn connected to the electronic circuitry 270 contained within the IMD enclosure by wires 304-307, respectively, and a feedthrough 308.

As noted earlier, during operation of the system 260, electrostatic charges tend to build up on the insulative surfaces 290-293 between and adjacent to the ring terminal contacts 282-284 on the connector assembly 276, and on the surfaces of the internal insulative seal sets 298-301, particularly during the voltage spikes appearing on the high voltage ring terminal contacts 282 and 283 and corresponding contacts 294 and 295.

Carbon nanotube-based coatings having the composition already described are applied to the sealing surfaces 290-293 and 298-301 to prevent the accumulation of such charges or to dissipate any accumulated charges. The use of carbon nanotube-based coatings which have negligible thickness, not only effectively dissipates the charge build up but also assures compliance with the connector size and tolerance specifications.

It will be evident that the invention is applicable to many lead variations, both unipolar and multipolar, and for both right side and left side placements; the lead configurations shown in the various drawing figures are examples only, and are not intended to be exhaustive. Thus, electrode configurations other than those described and shown herein may be employed pursuant to lead constructions well known in the art. For example, an alternative electrode arrangement may include additional ring stimulation and/or sensing electrodes as well as additional cardioverting and/or defibrillating coils. The invention is applicable to lead connector assemblies and associated IMD receptacles of all kinds, whether in-line, bifurcated, trifurcated, and so forth. Accordingly, while several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable medical lead for transmitting electrical signals between an implantable medical device and selected body tissue, the lead comprising:

a lead body comprising a distal end portion, a proximal end and an electrically insulating, elongated housing connecting said distal end portion and said proximal end, the proximal end of the lead body carrying an electrical connector assembly adapted to be electrically connected to the implantable medical device and the distal end portion of the lead body carrying at least one electrode electrically coupled to a terminal contact on the connector assembly by an electrical conductor, the elongated housing comprising at least one surface susceptible during use of the lead to the accumulation of electrostatic charges due to the electrical conductor riding in contact with the elongated housing, said at least one surface having an electrically conductive coating comprising carbon nanotubes to dissipate the accumulation of electrostatic charges;

wherein said housing comprises at least one lumen extending between the distal end portion and the proximal end of the lead body, said lumen containing the electrical conductor electrically coupling the at least one electrode to the terminal contact on the connector assembly; and wherein said at least one surface comprises at least a portion of a wall defining said at least one lumen.

2. The lead of claim 1 wherein:
said electrical conductor comprises a coil conductor.

3. The lead of claim 1 further comprising:
an insulating sealing surface on said electrical connector assembly having an electrically conductive coating comprising carbon nanotubes to dissipate accumulation of electrostatic charges.

4. The lead of claim 1 wherein:
said coating comprises a matrix selected from the group consisting of butylene tere phthalate, polyurethane, silicones, polyurethane/silicone copolymers and blends, and polystyrene, the carbon nanotubes being dispersed in said matrix.

5. The lead of claim 1 wherein:
said coating comprises a carbon nanotube loading of 0.005% to 4.5%, by weight.

* * * * *